United States Patent [19]
Caston et al.

[11] 3,972,991
[45] Aug. 3, 1976

[54] RADIOISOTOPIC ASSAY AND BINDER THEREFOR

[75] Inventors: Jesse Douglas Caston, Cleveland Heights, Ohio; Barton A. Kamen, Rockville Centre, N.Y.

[73] Assignee: Case Western Reserve University, Cleveland, Ohio

[22] Filed: Mar. 18, 1974

[21] Appl. No.: 451,875

[52] U.S. Cl. .............................. 424/1.5; 23/230 B; 424/1; 424/12
[51] Int. Cl.² ..................... G21H 5/02; G01T 1/16; A61K 43/00
[58] Field of Search .................. 23/230 B; 250/303; 424/1, 12

[56] References Cited
OTHER PUBLICATIONS

"Microbiologic Determination of Folic Acid Derivatives in Blood", vol. 20, No. 5, Nov., 1962, RB145.B6. pp. 609–616.

*Primary Examiner*—Leland A. Sebastian
*Assistant Examiner*—Christine M. Nucker
*Attorney, Agent, or Firm*—McNenny, Pearne, Gordon, Gail, Dickinson & Schiller

[57] ABSTRACT

There is provided a rapid and less costly radioisotopic assay for measuring the concentration of folate in blood serum. This procedure utilizes $^3$H-pteroylmonoglutamate, unlabeled 5-methyltetrahydrofolic acid, and a partially purified folate binder, such as for example a folate binder extracted from hog kidney. The procedure involves radioisotopically relating the bound amounts of a labeled folate and a known folate at various concentrations of the known folate in a system containing a predetermined amount of the labeled folate, a predetermined amount of the binder factor for the folates, and a predetermined amount of defolated test serum.

16 Claims, 8 Drawing Figures

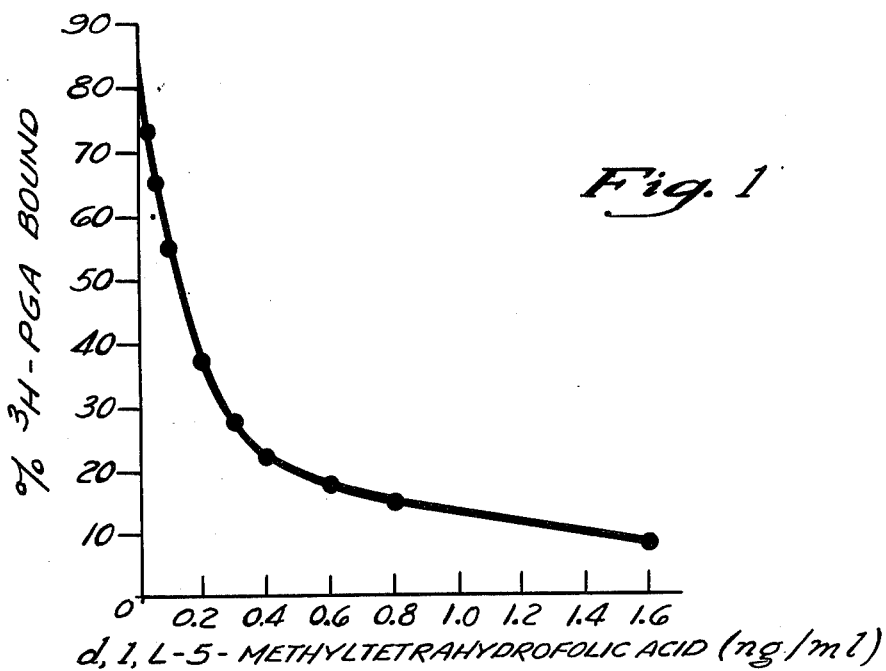
Fig. 1
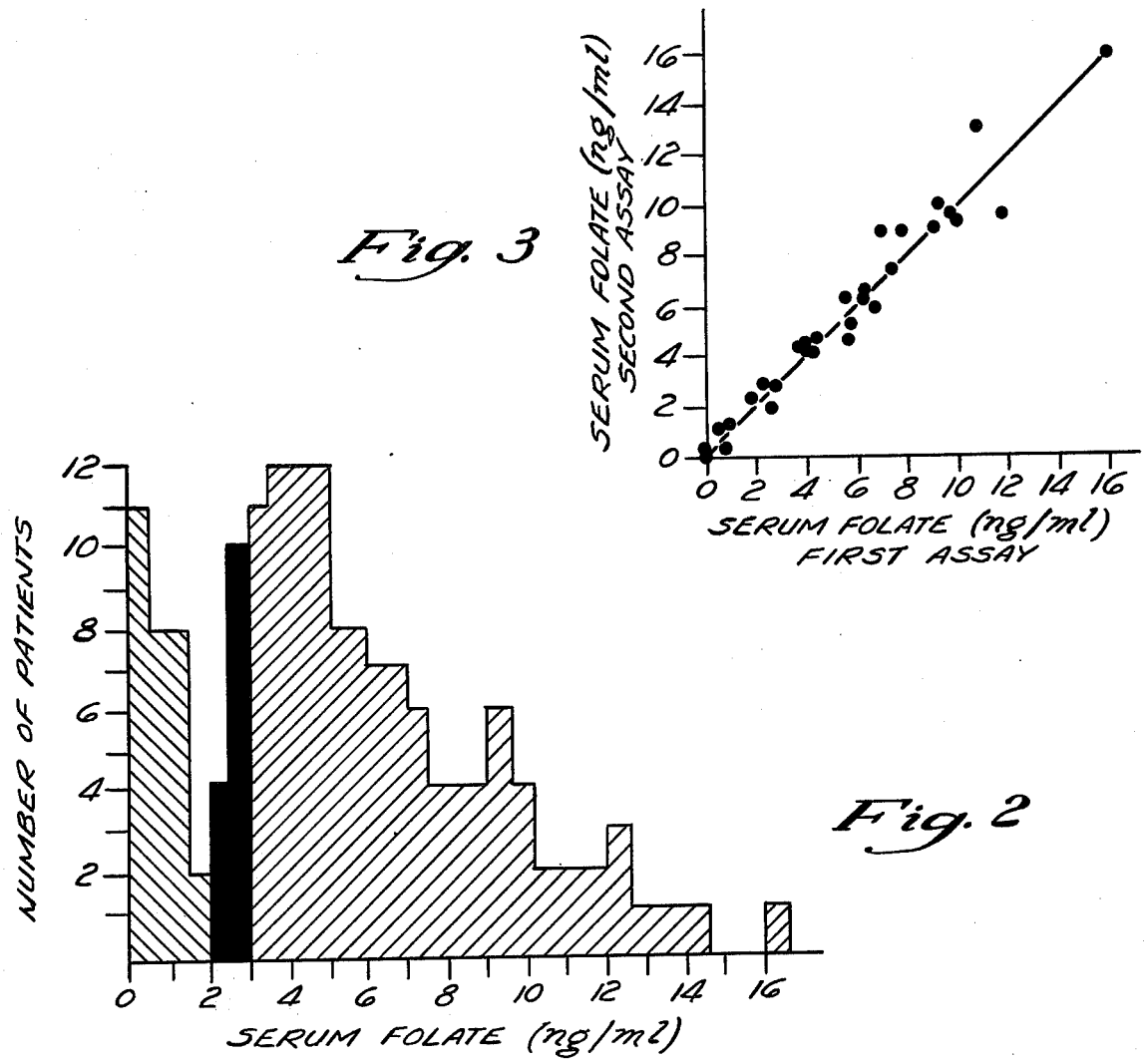
Fig. 3
Fig. 2

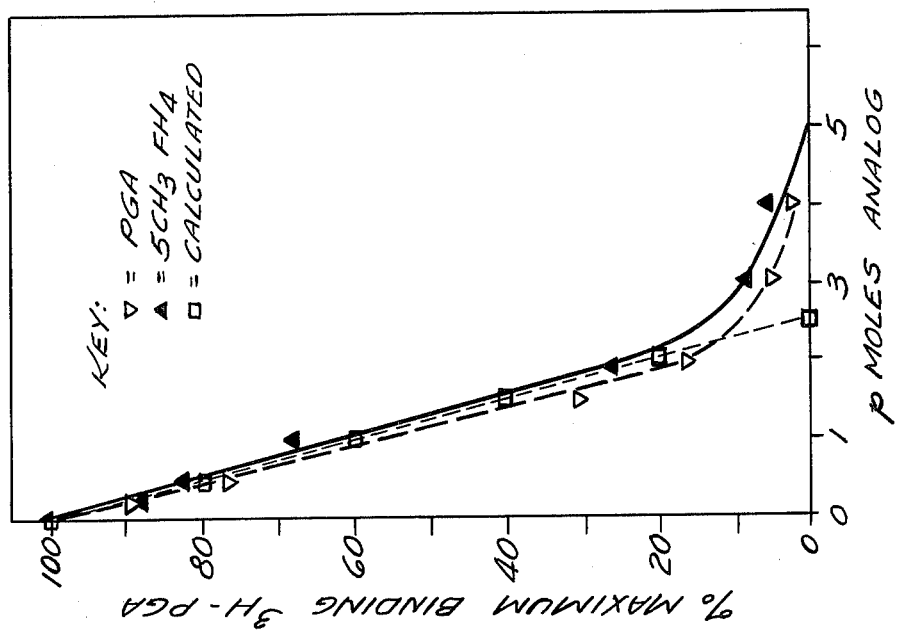
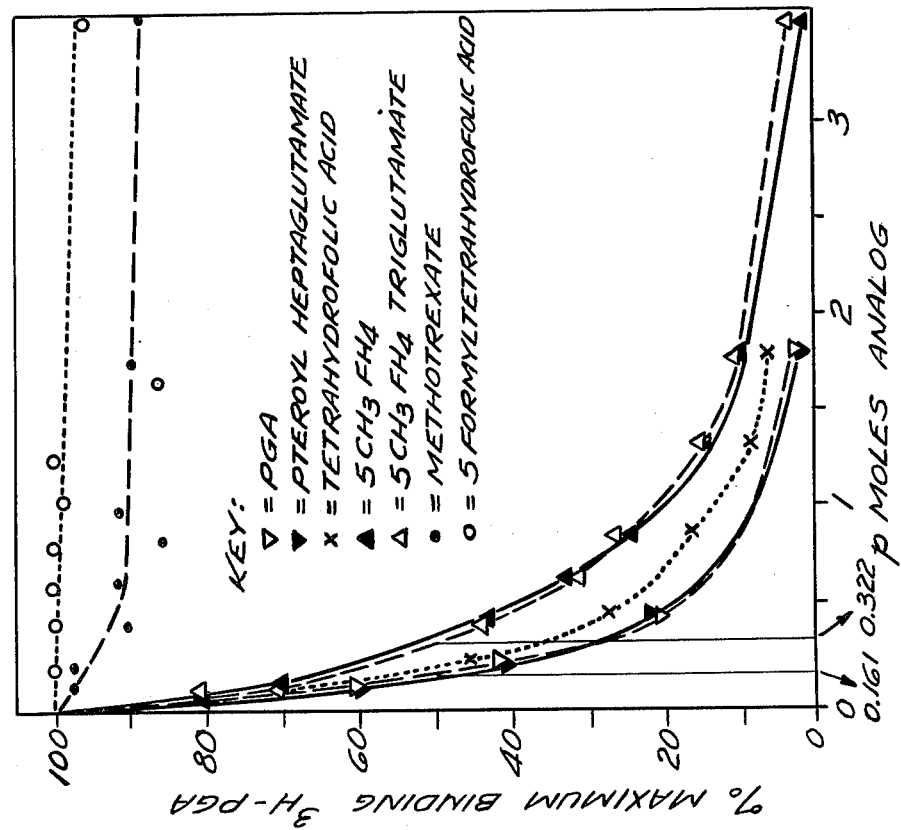

RADIOISOTOPIC ASSAY AND BINDER THEREFOR

BACKGROUND OF THE INVENTION AND PRIOR ART

The present invention relates, as indicated, to a competitive radioisotopic enzyme or biochemical cofactor assay for measuring the concentration of folate in serum. The term "folate" is well understood by those skilled in biochemistry. It is generic and includes not only the derivatives of pteroylmonoglutamic acid but also the salts and other neutralization products thereof. Whether a material is in the acidic or basic form will depend upon the pH of the medium in which it is found. Thus, the term folate includes substituted derivatives of pteroylmonoglutamic acid and the polyglutamate forms as well as esters, salts and other such derivatives involving not only the carboxyl group but also other points of substitution on the molecule. It is often helpful to know the serum folate concentration in order to confirm the etiology of a patient's anemia. Presently known microbiological assays for measuring the serum folate concentration, however, are time-consuming and, like other microbiological assays, are affected by antimicrobial and antineoplastic agents which may be present in the serum sample. Reference may be had to the work by Herbert entitled, "Aseptic Addition Method for Lactobacillus Casei of Folate Activity in Human Serum," J. Clin. Path. 19: pp 12–16, 1966; and Grossowicz et al, "Microbiologic Determination of Folic Acid Derivatives in Blood," appearing in Blood 20, pp 609–616, 1962. The present process is distinguished from these microbiological assays in utlizing a radio assay procedure characterized by a direct competitive binding between a labeled folate and a second folate, in one case the second folate being known and in the second case the second folate being a serum folate, whereby the concentration of folate in the serum may be determined. This assay may be completed in a morning's work and the results obtained by the end of the day. This assay employs $^3$H-pteroylmonoglutamate (hereinafter identified as $^3$H-PGA) as the labeled folate, d,1,5-methyltetrahydrofolic acid (hereinafter called $5CH_3FH_4$) as a known folate, a partially purified folate binder extracted from hog kidney or other suitable animal organ. This assay is sensitive to 25 picograms of $5CH_3FH_4$, the main serum folate (see Herbert et al, "Studies on the Identification of a Folate Compound of Human Serum," J. Clin. Invest. 41: pp 1134–1138, 1962). Unlike microbiological assays, the present assay is unaffected by antimicrobials or antineoplastic agents such as Methotrexate (amethopterin), 4-(amino-$N^{10}$-methylpteroylglutamic acid). Reference may also be had to Rothenberg et al, "A Radio Assay for Serum Folate: Use of a Two-Phase Sequential-Incubation, Ligand-Binding System," New England Journal of Medicine 286: 1335–1339, 1972.

Binders of pteroylmonoglutamate (PGA) and some of its derivatives have been described in milk, serum from some pregnant women, folate deficient patients, and serum from some patients with a malignant disease. Folate binders may be extracted from various animal organs, particularly the kidneys and pancreas. Spleen, liver, heart and muscle tissue, while they do contain minor amounts of material useful as binder, do not contain such material in commercially significant amount. The procedure of extraction is in any case the same. Best results have been secured with hog kidney binder factor. Accordingly, the description of the procedure for extracting the binder factor from animal organs will be exemplified by reference to the procedure for extracting binder factor from hog kidneys. It will be understood that the same procedure may be utilized for preparation of binder factors from such other organs.

The hog kidney binder preparation has proved very useful in setting up a competitive ligand binding assay for measuring folate, especially serum folate. In addition, this binder appears to offer a good model system for study and comparison to folate binders found to be in the serum of patients with certain diseases.

BRIEF DESCRIPTION OF THE DRAWINGS

In the annexed drawings,

FIG. 1 is a typical standard curve showing the relationship of percent $^3$H-PGA bound to various concentrations of $5CH_3FH_4$ in ngs.

FIG. 2 is a histogram showing the distribution of serum folate concentration in the total population tested.

FIG. 3 demonstrates the relationship between values obtained for serums assayed in duplicate on two different days.

FIGS. 6A and 6B show the specificity of hog kidney binder folate factor for several folate derivatives.

DETAILED DESCRIPTION OF THE PREPARATION OF MATERIALS AND THE METHODS EMPLOYED

Figure 4:
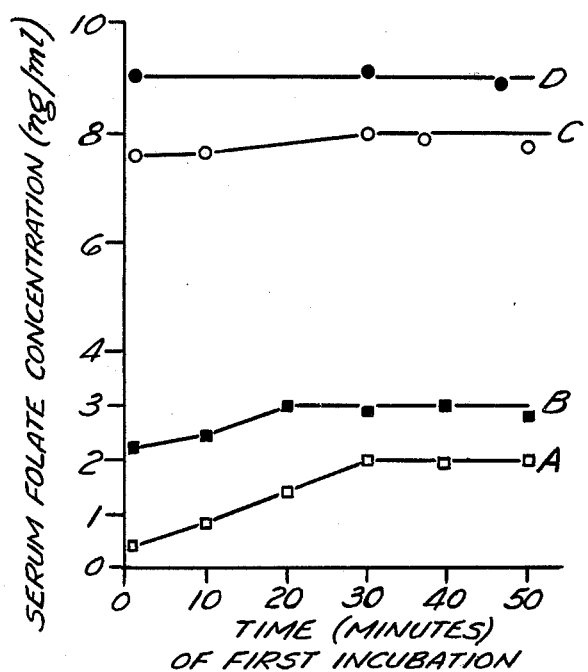
FIG. 4 shows the serum folate values obtained for several sera as a function of the equilibration time.

A hog kidney folate binder composition is conveniently prepared from fresh, defatted hog kidney which has been homogenized in three volumes (w/v) of 0.05 M citric acid or, alternatively, commercially available (Sigma chemical) acetone extracted hog kidney powder is suspended in 10 volumes (w/v) of 0.05 M citric acid and stirred for one hour at room temperature. The volume of citric acid may range from 10 – 15. If necessary, the solution is adjusted to pH 3.5 with 5 N hydrochloric acid. After addition of 2-mercaptoethanol to a final concentration of 5 mM (millimolar) finely divided activated charcoal (Norit A) is then stirred into the suspension to a concentration of from about 2% to about 5% (w/v).

The purpose of the charcoal is to remove by absorption folate occurring in the kidney binder source from the system. It has been found that concentrations on a w/v basis of as low as about 2% give excellent yields of binder and effectively remove folate. Higher concentrations of charcoal tend to remove binder as well as folate. Hence the lower charcoal concentrations are to be preferred in terms of yield of binder. Any other method of separating molecular entities without destroying the binder factor having molecular weights on the one hand from 400 to about 1000 (e.g. folates) from molecular entities having molecular weights of the order of 40,000 (e.g. binder) may be used such as chromatography, molecular sieves, etc.

The mercaptoethanol has been found to improve solubilization of the binder factor and the yield without affecting the assay. Its presence is optional. After standing for a period of from 5 to 20 hours at 4°C, the mixture is centrifuged for approximately 30 minutes at 13,000 × G at 4°C to remove the charcoal and any precipitated material. The supernatant liquid is adjusted slowly to pH 7.4 with N NaOH and then mixed with an equal volume of absolute ethanol at −20°C. After standing for a period of 4 hours at −20°C, the precipitate is collected by centrifugation at 13,000 × G and discarded. The resultant supernatant liquid is brought to a final ethanol concentration of 75% with absolute alcohol and allowed to stand overnight at −20°C. The precipitate is collected by centrifugation at 13,000 × G, dried at room temperature and suspended in a volume of 0.05 M potassium phosphate buffer at a pH of 7.6, the amount of phosphate buffer being about 5% of the initial volume. The suspension is stirred slowly for 20 minutes at 4°C and then centrifuged for 10 minutes at 10,000 × G at 4°C and the supernatant fluid saved. If any red color is still present in the precipitate, a small volume of phosphate buffer is added and the extraction procedure repeated. The resultant straw to red colored solution represents about a 50% yield of the total binding capacity of th initial citric acid extract and shows a 20 – 30 fold increase in specific acitivity over the citric acid extract.

which cannot be removed by simple charcoal absorption techniques.

The standard or known folate (d,1,L-5-methyltetrahydrofolic acid) (Sigma Chemical) is dissolved in 0.05 M potassium phosphate buffer pH 7.6 and then brought to 0.1 M with 2-mercapto-ethanol. Here the mercapto-alcohol acts as a stabilizer for the folate or folic acid. The purity of the $5CH_3FH_4$ is determined spectrophotometrically and the concentration is determined by employing an $\epsilon^{1\%}_{cm}$ at 290 nm of 665 (Gupta et al, "Preparation and Properties of Crystalline 5-Methyltetrahydrofolate and Related Compounds," Arch. Biochem. Biophys. 120, pp 712–718, 19670. The stock solution (approximately 5 micrograms per ml) is frozen in small aliquots at −80°C until use. This solution has proved to be stable for a period of at least 6 months.

High specific activity $^3$H-PGA (15–50 Ci/m mole; Amersham Searle) is conveniently utilized as the tracer or labeled compound. It is dissolved in 20% ethanol and stored at −80°C. For use in the assay, the stock solution is diluted 1:100 in potassium phosphate buffer (0.05 M pH 7.6).

Finely divided activated charcoal coated with albumin is prepared by mixing equal volumes of a 5% powdered activated charcoal (Norit A) suspension (w/v, in distilled water) and a 1% aqueous solution of bovine albumin (Fraction V of Cohn). This suspension is sta-

| | Protein Conc. mg/ml | Total Vol. Ext. ml | Total Protein mgs | Binding Capacity for PGA (n moles) | Specific Activity n moles PGA/mg Protein |
|---|---|---|---|---|---|
| Crude citric acid extract | 7.6 | 3500 | 26,600 | 29.7 | 0.0011 |
| Ethanol ppt. (50–75%) | 6.17 | 75 | 462.7 | 13.6 | 0.029 |

It has been found that fresh hog kidney treated according to the method of Iwai et al, "Blood Folic Acid Studies VII Purification and Properties of the Folic Acid Precursors of Human Erythrocytes," J. Biol. Chem. 239: pp 2365–2369, 1964, for the preparation of conjugase also contains a folate binder. Such preparations, however, are not as stable as those made from the preferred acetone powder. Properties of the folate binder as presented herein are determined on preparations made from acetone powder.

Assays in accordance with the present invention are carried out preferably in a potassium phosphate-ascorbate-serum buffer (herein identified as KPAS). This buffer solution is prepared by diluting pooled normal human serum 1:10 in 0.05 M potassium phosphate buffer (pH 7.6) and adding 2.0 mg ascorbic acid per ml to the final solution. Pooled normal human serum is formed blending together a plurality of samples of serum from normal human blood samples. Prior to using the pooled serum, it is treated with powdered activated charcoal (Norit A) to remove endogenous folate. This is accomplished by adding 15.0 mg of activated charcoal per milliliter of serum, slowly stirring the suspension for 10 minutes at 4°C and then centrifuging to remove the charcoal. This yields a so-called "folate-free" serum which is frozen in small aliquots at −80°C until used in the assay buffer. As will appear hereinafter bound folate may occur in human serum ble for at least one month when stored at 4°C. In this connection, it should be noted that any material of relatively high molecular weight may be used to coat the charcoal in place of the bovine albumin such as, for example, hemoglobin, or dextran (which is a polysaccharide) of suitable molecular weight range, i.e. 10,000 to 50,000.

The samples are counted using standard liquid scintillation techniques well known in the art in a scintillaion fluid which, for example, may be prepared by mixing equal volumes of toluene containing 13.7 grams of 2,5-diphenyloxazole (PPO/1, scintillation grade) and 0.28 grams of 1,4-bis-2-(4-methyl-5-phenyloxazolyl) benzine (POPOP/1, scintillation grade), and a nonionic wetting agent, such as an alkylene oxide condensation product with an alkyl phenol, e.g. nonyl phenol plus 9 mols ethylene oxide (Triton X-100). Sufficient counts are collected to obtain a counting error of 4% or less.

Blood to be assayed for folate is obtained by venapuncture and allowed to clot at room temperature. The serum is collected by centrifugation and 5 milligrams of ascorbic acid per milliliter of serum is added. When the serum is collected in this manner and stored at −20°C the folate level remains stable for at least 3 months.

As indicated above, a characterizing step of the present invention is the determination of the standard curve. The prior art has previously determined that the principal human serum folate is $5CH_3FH_4$ (Herbert et al "Studies on the Identification of a Folate Compound of Human Serum" supra) and it is, therefore, used to compete for PGA binding sites in the hog kidney binder preparation. By using increasing amounts of 5CH₃FH₄ and a constnat known amount of ³H-PGA and a constant known amount of the binder factor, preferably with an aliquot of defolated pooled serum as a blank, it is possible to relate the percent decrease of the labeled folate/binder complex formed (% ³H-PGA bound) to the different known concentrations of 5CH₃FH₄. To determine the concentraion of folate in a given serum sample, therefore, it is only necessary to compare the percent of ³H-PGA which is bound when an aliquot of serum is added to the incubation mixture in replacement of the aliquot of defolated pooled serum, if such is used, to a series of known 5CH₃FH₄ concentrations represented in a standard curve. Reference may be had to FIG. 1 which is a typical example of a standard curve determined in accordance with this procedure.

In these tests, the incubation mixture contained 200 picograms of ³H-PGA in 20 – 40 microliters, 0.1 ml of 5CH₃FH₄ solution (the stock solution being serially diluted in potassium phosphateascorbate buffer to the appropriate concentration) and 0.1 ml of binder solution in enough KPAS so that the final volume of the incubation mixture was 1.0 ml. To obtain a high degree of sensitivity, the binder is diluted so that 0.1 ml is enough to bind 70 – 80% of the ³H-PGA when there is no competing 5CH₃FH₄ present. Since the assay in accordance with the present invention is of a competitive binding type, the binder is added last to the solution of ³H-PGA and 5CH₃FH₄ in the KPAS. Prior to adding the binder, the reaction mixture is allowed to incubate for 30 minutes at 4°C in the dark in order to permit the equilibration of the ³H-PGA and the 5 CH₃FH₄ in the KPAS. After the addition of binder, the reaction is incubated for an additional 45 minutes at room temperature and in the dark.

Free and bound ³H-PGA are separated at the end of the incubation by placing the tube on ice and adding 1.0 ml of the cold albumin coated powdered activated charcoal suspension which absorbs the free ³H-PGA. After adding the charcoal suspension, the tubes are allowed to stand for 2-3 minutes and then centrifuged for 10 minutes at 6000 × G at 4°C to pelletize the charcoal. An aliquot of the clear supernatant fluid from the centrifugation step is dispersed in and counted in 15.0 ml of the scintillation fluid above described.

A charcoal control (hereinafter called cc) is prepared by substituting 0.1 ml KPAS for binder in one tube. The counts remaining in the supernatant liquid after treatment with the charcoal suspension represents the nonabsorbable tritum counts. Usually this is found to be in the range of from 5% to 7% of the total counts incubated. If the PGA was not at least 85% pure as tested by the zinc sulfate precipitation test described in Rothenberg et al., New England Journal of Medicine 286. 1335–1339, 1972, a second control is prepared. This control, hereinafter called maximum binding control or (mbc), is prepared by incubating the ³H-PGA with an aliquot of undiluted binder prepared as above described. The counts per minute (cpm) in the supernatant fluid after charcoal treatment represents the maximum number of counts that can be bound. The net cpm bound in any sample is calculated by subtracting the cc value from the total number of cpm in the sample. The percent ³H-PGA bound in a given sample is calculated in accordance with the following formula:

$$\% \ ^3H\text{-}PGA \ \text{bound} = \frac{cpm \ \text{sample} - cc}{cpm \ mbc - cc} \times 100$$

The standard curve is constructed by calculating the percent ³H-PGA bound and plotting this as a function of the 5CHFH₄ concentration to yield a curve such as shown in FIG. 1. Since the tritiated folate is unstable, it is preferred practice in all cases to determine an "mbc".

In the assay of human serum, routinely, 0.1 ml aliquots of serum were analyzed. The samples were added to 0.8 ml of a potassium phosphate-ascorbae buffer (KPA) which is the same as KPAS but without the defolated serum, and containing 200 picograms of ³H-PGA. As described above, the samples are incubated for 30 minutes after which time the binder is added. The balance of the procedure is the same as that followed in determining the standard curve shown in FIG. 1.

The validity of the assay was determined by (1) assaying sera with the sequential ligand binding assay described by Rothenberg supra, (2) assaying sera with the L. casei method described by Herbert in J. Clin. Path. 1912–16, 1966, (3) adding known amounts of 5CH₃FH₄ and calculating the percent recovery, and (4) by assaying sera which had been deproteinized by heating in a test tube immersed in a boiling ascorbate-phosphate buffer.

Test results which have been obtained are as follows: FIG. 1 as indicated above illustrates a typical standard curve obtained when the percent ³H-PGA bound is plotted as a function of the concentration of 5CH₃FH₄.

In one evaluation, a total of 165 different serum samples were assayed using the method of the present invention. 30 serum samples were from patients with a megaloblastic or macrocytic anemia. The remaining samples were from "normal" subjects. FIG. 2 in the annexed drawings is a histogram showing the distribution of serum folate concentration in the total test population. The mean serum folate concentration in patients with either megaloblastic (as determined by bone marrow morphology) or macrocytic anemia (a mean corpuscular volume greater than 120 cubic microns; 86 – 93 being normal) but with normal serum vitamin $B_{12}$ levels was 0.74 ng/ml plus or minus 0.17 ng/ml (standard error of the mean, S.E.M.). The range was from 0.0 to 1.5 ng/ml. The mean serum folate concentration in the normal population consisting of house staff, medical students, undergraduates and research personnel) was 6.1 ng/ml plus or minus 0.31 ng/ml (S.E.M.). The range was from 1.5 to 16.0 ng/ml. In the presumed normal population 14.2% exhibited folate levels between 1.5 and 3.0 ng/ml. This population had a mean corpuscular volume of 97 cubic microns tested over 20 samples with a range of from 95 cubic microns to 103 cubic microns whereas the mean corpuscular volume in the normal population (i.e. folate 3.0 ng/ml) was 91 cubic microns with a range of from 86 cubic microns to 93 cubic microns over 25 samples.

The mean percent variation for samples assayed in duplicate on the same day was 3.1%.

FIG. 3 illustrates the relationship between values obtained for serums assayed in accordance herewith in duplicate on two different days. The means variation was 4.6%.

The recovery of exogeneously added $5CH_3FH_4$ is shown in Table II below. The low recovery obtained in serum with low endogenous level of folate suggests the presence of unsaturated binder in the patients' sera.

TABLE II

Recovery of $5CH_3FH_4$ Added to Serum Samples

| Sample | Endogenous Folate (ng/ml) | Exogenous $5CH_3FH_4$ (ng/ml) | Expected Value (ng/ml) | Actual Value (ng/ml) | % Recovery |
|---|---|---|---|---|---|
| 1 | 2.7 | 4.3 | 7.0 | 6.2 | 88.5 |
| 2 | 8.4 | 4.3 | 12.7 | 13.6 | 100.6 |
| 3 | 4.2 | 4.3 | 8.5 | 12.0 | 141.1 |
| 4 | 4.6 | 4.3 | 8.9 | 8.5 | 97.7 |
| 5 | 9.0 | 4.3 | 13.3 | 12.0 | 90.5 |
| 6 | 6.2 | 4.3 | 10.5 | 12.0 | 114.0 |
| 7 | 6.2 | 8.6 | 14.8 | 16.0 | 108.1 |
| 8 | 5.4 | 8.6 | 14.0 | 15.2 | 108.5 |
| 9 | 5.4 | 8.6 | 14.0 | 12.4 | 88.6 |
| 10 | 4.6 | 8.6 | 13.2 | 12.6 | 95.5 |
| 11 | 1.3 | 8.6 | 9.9 | 3.6 | 36.4 |
| 12 | 0.7 | 8.6 | 9.3 | 4.2 | 45.2 |

The $5CH_3FH_4$ was diluted in phosphate-ascorbate buffer and added in 0.01 ml to 1.0 ml aliquots of serum. Some of the samples were then refrozen prior to assaying.

$$\% \text{ Recovery} = \frac{\text{assayed value}}{\text{expected value}} \times 100$$

As stated above, the $^3$H-PGA was allowed to equilibrate with the serum prior to adding the binder. The serum folate values obtained for several sera as a function of the equilibration time are shown in FIG. 4. It was found that 30 minutes gave a maximum response and accordingly this is the time period used in the assay. With reference to FIG. 4, the legends A, B, C, and D indicate serum from different patients. While it is not presently known why some examples show an increase in folate concentration as shown by examples A and B particularly, nevertheless in order to assure accurate determination over the broadest spectrum of concentrations, it has been determined that incubation for a period of at least about 30 min. is to be preferred. On the other hand, if incubation is prolonged for in excess of about 90 minutes, for example, a destructive action sets in and the readings obtained for folate concentration begin to fall. Incubation for from 30 to 60 minutes is preferred.

A comparison of whole and extracted sera is presented in Table III below.

TABLE III

Comparison of Serum Folate Levels Determined by Assaying Whole Serum and Serum Extracts

| | Folate Concentration (ng/ml serum) | |
|---|---|---|
| Sample | whole serum | serum extract or denatured serum |
| 13 | 0.0 | 1.0 |
| 14 | 3.5 | 5.0 |
| 15 | 14.6 | 15.5 |
| 16 | 5.2 | 6.0 |
| 17 | 4.1 | 6.0 |
| 18 | 3.8 | 5.0 |
| 19 | 3.1 | 4.0 |
| 20 | 10.0 | 13.0 |
| 21 | 0.8 | 2.2 |

Serum extracts were prepared by diluting serum 1:5 in KPA to which an additional 5.0 ng/ml ascorbic acid had been added. The tubes were then placed in a boiling water bath for five minutes to denature the serum. The coagulated protein was removed by centrifugation. An aliquot of the clear supernatant was assayed for its folate content. Since the protein had been extracted from the sample, the standards were prepared in KPA instead of KPAS so that assay conditions would be identical. Sample 13 represents results obtained from assaying charcoal treated serum.

Although charcoal treated pooled normal human serum had no folate activity when measured as whole serum, some folate activity was released when the serum was extracted or denatured. This is a most significant discovery as will later appear.

Table IV below shows the comparison of the sequential ligand binding and competitive binding radioisotopic assays for a number of sera over a wide range of values.

TABLE IV

Comparison of the Direct Competitive and Sequential Assays

| | ng Folate/ml Serum | |
|---|---|---|
| Sample | Direct Competitive Assay | Sequential |
| 22 | 4.0 | 3.8 |
| 23 | 6.5 | 6.3 |
| 24 | 15.0 | 17.0 |
| 25 | 9.7 | 11.0 |
| 26 | 2.5 | 2.3 |
| 27 | 2.2 | 1.7 |
| 28 | 5.4 | 5.2 |

The sequential assay was performed according to the method of Rothenberg et supra; the only difference was the substitution of the hog binder extract for mi binder. In this particular series of assays 20 microliter samples of serum were assaye The results presented represent the mean of triplicate determinations.

Figure 5:
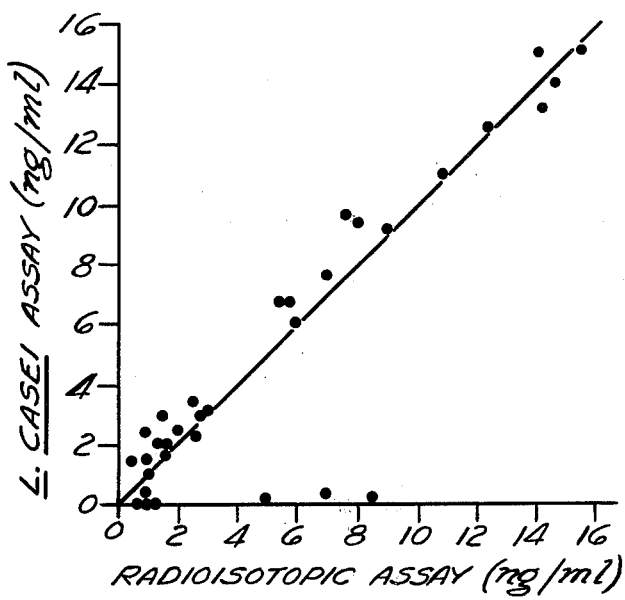
FIG. 5 demonstrates the relationship between the present assay procedure and the prior art L. casei microbiological assay.

FIG. 5 demonstrates the relationship between the present assay procedure and the *L. casei* microbiological assay described by Herbert, supra, for the determination of serum folates. The microbiological assay was consistently higher by an arithmetic rather than geometric constant. This difference in the two assays is reflected in the normal ranges established for each assay. The *L. casei* assay has a normal range of from 4 to 20 ng/ml whereas the "normal range" in the radioisotopic assay is 3 to 16 ng/ml. A suitable process for the preparation of the hog kidney folate binder factor is given above.

DISCUSSION OF RESULTS

The assay procedure of the present invention utilizes commercially available, high specific activity $^3$H-PGA and is, as indicated above, sensitive to 25 picograms of unlabeled $5CH_3FH_4$. The serum folates are determined by comparing the degree of competitive inhibition of radio activity observed when an aliquot of serum is added to the mixture of $^3$H-PGA and folate binder, to the inhibition observed when known amounts of $5CH_3FH_4$ are added to the incubation reaction. 5-methyltetrahydrofolic acid ($5CH_3FH_4$) is used as the reference folate because it has been shown to be the major serum folate (Herbert et al, J. Clin. Invest. 41: 1134–1138, 1962, supra). Additionally, had PGA been used instead of $5CH_3FH_4$ to ascertain the standard curve of FIG. 1, falsely lower levels for serum folates would have resulted because of the greater competition by unlabeled PGA with respect to $5CH_3FH_4$ for th binding sites in the binder factor. This preferential binding of PGA by the hog kidney binder has also been observed in the preparations of folate binder extracted from milk. (See Ford et al, "The Folate Binding Protein in Milk," J. Dairy Research 36: 435, 1969.)

However, unlike the milk binder, when the hog kidney folate binder is employed in this sequential binding assay as described by Rothenberg, supra, i.e. when the unlabeled folate derivative is incubated with the binder factor prior to the addition of the $^3$H-PGA, there was only from 5% to 10% displacement of bound $5CH_3FH_4$ by the PGA even when incubated at room temperature.

Thus, although there is an apparent preferential binding of PGA based upon direct competition studies, the lack of displacement of bound $5CH_3FH_4$ made it possible to use a one-step competitive assay as opposed to the sequential ligand binding assay of the prior art and still obtain a sensitivity for 25 picograms of $5CH_3FH_4$. The observations (1) that charcoal treated serum has folate activity after it has been extracted, and (2) that when $5CH_3FH_4$ recovery experiments are performed using sera with initially low endogenous folate levels yield a poor recovery of added folate, suggest that there is a pool of bound folate in human sera which is not detected with a radioisotopic assay unless the serum is extracted prior to assay.

In this regard, Markkenen and Peltola, "Carrier Proteins of Folic Acid Activity in Human Serum," Acta Haemat 45: 106–111, 1971, have fractionated human serum and found three areas of folic acid activity. Two of these three areas are in regions of high molecular weight proteins. It has now been found that some of the folic acid activity is firmly bound in one of these two fractions. Evidence supporting the existence of a "bound folate pool" in human blood serum is seen by comparing the results obtained from assaying whole serum and extracted or denatured sera in Table III above. Since the increase in the final serum concentration is an arithmetic constant (0.0 to 3.0 ngs) and not directly proportional to the whole serum folate value, these results led to the discovery of the existence of a small bound pool of folate. The extent of the bound pool, or its variation from a norm determined for an individual, appears capable of major diagnostic significance. The amount of bound pool of folate in serum is determined by subtracting from the total folate determined using denatured serum, the amount of free folate determined using undenatured serum.

It should be reemphasized at this point that PGA and any of its derivatives (which can compete for binding of PGA in the hog kidney folate binder factor) loosely associated with serum proteins, mainly albumin, are detected by the radioisotopic assay as evidenced by the recovery experiments. In this connection reference may be had to Elsborg, "Binding of Folic Acid to Human Plasma Proteins," Acta Haemat 48: 207–212, 1972; and Johns et al, "The Metabolism of Tritiated Folic Acid in Man," J. Clin. Invest. 40: 1684, 1961. The bound, noncharcoal extractable folate activity discussed above may represent folate bound to serum folate binder or binders analogous to those that have already been described in connection with milk, in the serum, and in leukocytes from patients who are pregnant or have chronic granulocytic leukemia, and in hog kidney. In these respects, reference may be had to Ghitis, "The Folate Binding in Milk," Am. J. Clin, Nutr. 20: 1015–1024, 1967; Ghitis et al, "Binding of Folic Acid and Derivatives by Milk," Am. J. Clin. Nutr. 22: 156–162, 1969; and Rothenberg et al, "Further Observations on the Folate Binding Factor in some Leukemic Cells," J. of Clin. Invest. 50: 719–726, 1971.

The diagnostic screening value of assaying whole serum is not adversely affected by this bound folate as evidenced by the correlation between the hematologic findings and the measured serum folate. However, it must be recognized that the whole serum value obtained in accordance with the present invention is an indication of the serum folate concentration relative to a $5CH_3FH_4$ standard but does not necessarily equal the total serum folate. A total serum folate can be obtained by first extracting the serum samples. Since the nature of the bound folate is not known, the value obtained would only be a folate concentration relative to $5CH_3FH_4$. If the bound folate is an oxidized derivative of PGA, then it would exhibit greater competition than $5CH_3FH_4$ on a molar basis and therefore result in falsely high values. Since there is a good clinical correlation between the hematologic findings and the whole serum folate level as assayed by the method herein described, this procedure serves as a rapid and inexpensive test aiding in the diagnosis of folate deficiency.

Among the various folate binder factors investigated, that derived from hog kidney appears to be vastly superior. In this regard, the specificity of the folate binder factor was examined by using unlabeled folate derivatives to compete with $^3$H-PGA, $^3$H-methotrexate (MTX) or $^{14}$C-5-methyltetrahydrofolic acid ($5CH_3FH_4$) for binding sites. Direct binding studies with $^3$H-MTX (13Ci/mmole) showed that its binding affinity was at least 500 times less than that of $^3$H-PGA. Results obtained with $^{14}$C—$5CH_3FH_4$ were essentially the same as those obtained with $^3$H-PGA. However, because $^{14}$C—$5CH_3FH_4$ had a low specific activity, few competitive experiments were undertaken. Even so, it can be stated that the extract bound more than 90% of the available $^{14}$C—$5CH_3FH_4$, indicating that both the dextro and levo-forms of the reduced folate were bound. Similar results have been reported for the milk binder. With the hog kidney binder, a high degree of competition by $d$, 1-tetrahydrofolic acid (FIG. 6 and by N-10, formyltetrahydrofolic acid (not shown) for PGA binding sites was also observed. These results, however, do not reveal whether there is some difference in binding the dextro and levo-forms of reduced folates. The lack of equimolar competition of tetrahydrofolic acid and its derivatives for $^3$H-PGA binding sites may have been due to the presence of the dextro isomer.

In determining the data for FIG. 6, the first portion of FIG. 6 (FIG. 6A) shows the direct competition for PGA binding sites in hog kidney folate binder. The reaction mixture contained 0.225 pmoles $^3$H-PGA (54 Ci/mmole), unlabeled folate derivatives as indicated, enough hog kidney binder factor to bind about 0.18 pmoles PGA, 1 micromole of 2-mercaptoethanol, 50 micromoles of potassium phosphate, a final pH of 7.6, in a total volume of 1.0 ml. The reaction was started by addition of folate binder and allowed to proceed for 30 minutes at room temperature in the dark. The reaction was stopped by placing the tubes on ice and adding 1.0 ml of a suspension of powdered activated charcoal coated with albumin. After 2 to 3 minutes on ice, the tubes were centrifuged at 6000 × G for 10 minutes at 4°C to remove the charcoal absorbed "free" folate. 1.0 ml of the clear supernatant fluid which contained the folate/binder complex was counted by liquid scintillation spectroscopy according to known procedures. Charcoal controls prepared by substituting buffer for binder in one series of tubes were prepared to determine the number of counts not removed by the charcoal. Percent maximum binding was calculated by the formula $$\frac{cpm \text{ in sample tube} - cc}{cpm \text{ in zero tube} - cc} \times 100$$

The second portion of FIG. 6 (FIG. 6B) shows the effect of sequential addition of unlabeled folate derivatives and $^3$H-PGA. The binding conditions were similar to those used in obtaining the data appearing in FIG. 6A except that 3 pmoles of $^3$H-PGA was added to the reaction containing enough binder factor to bind about 2.5 pmoles of PGA. The binder was preincubated for 30 minutes in the dark at room temperature with unlabeled folate derivatives as indicated. Then the $^3$H-PGA was added and the reaction allowed to continue for an additional 30 minutes and then stopped and counted as in obtaining the data for FIG. 6A. Similar results were obtained when $^{14}$C-5 methyltetrahydrofolic acid was used instead of $^3$H-PGA.

In contrast with known milk binder factors wherein PGA can displace bound $5CH_3FH_4$, FIG. 6B illustrates the substantial absence of such displacement when the hog kidney binder factor of the present invention is employed. The calculated curve of FIG. 6B depicts the relationship to be expected by balancing on a molar basis the binding capacity of the hog kidney binder factor with the known pmoles of folate analog added in the absence of any displacement. It is apparent that the hog kidney binder factor binds the $5CH_3FH_4$, which is the main serum folate, with a degree of tightness that bars significant displacement by the $^3$H-PGA. Even when incubated at 21°C, a temperature which is favorable for the displacement reaction with milk binder factor, less than 10% of the bound $5CH_3FH_4$ was displaced by PGA. The hog kidney binder factor thus differs from other high affinity folate binder factors such as those found in milk and in serum and in leukocytes of some patients with chronic granulocytic leukemia.

The PGA curve of FIG. 6B further illustrates that the tightness of binding of the hog kidney binder factor with PGA and $5CH_3FH_4$ are approximately equal. Accordingly, the hog kidney binder factor of the present invention enables the use of a competitive (one-step) assay for measuring the concentration of folate in serum.

Referring to both FIGS. 6A and 6B, the sensitivity of the hog kidney binder factor to folate derivatives is illustrated. Most particularly, the sensitivity or affinity of the binder factor for the folate derivatives relative to the tritiated PGA tracer material is illustrated by the relatively steep slopes of the curves. Accordingly, the accuracy of the correlation between the test serum count and the standard curve is enhanced.

The hog kidney binder factor has demonstrated a preference between PGA and $5CH_3FH_4$ on the order of 1:2. This is illustrated by reference to FIG. 6A and consideration of the 50% maximum binding values. Specifically, in order to achieve 50% inhibition, approximately 0.16 pmoles of PGA is required whereas about 0.32 pmoles of $5CH_3FH_4$ is required to achieve the same inhibition. In contrast with the 1:2 sensitivity characteristic of the hog kidney binder factor, a milk binder factor is from 7 to 10-fold less sensitive to the $5CH_3FH_4$. In the context of FIG. 6A, a milk binder factor would display a 50% inhibition upon the addition of about 1.1 to 1.6 pmoles of $5CH_3FH_4$. Thus, it is apparent that the milk binder factor results in a less desirable curve (e.g. less steep) for purposes of correlation. The inaccuracies introduced by the rather large sensitivity variation of a milk binder factor in combination with the inadequate binding tightness characteristics render the milk binder factor unacceptable in a competitive (one-step) assay.

The sensitivity of the hog kidney binder factor also permits the assay to be carried out with a relatively small serum sample. In many instances, the size of the sample is limited by practical considerations as when an infant patient is involved. Moreover, it is desirable to employ a relatively small sample since this minimizes the secondary or nonspecific effects which may arise.

Preincubating a 1.0 ml aliquot of binder extract from hog kidney having a binding capacity of 25 ng PGA/ml, with 1.0 ml RNase (Worthington, 2 micrograms per ml) or with DNase I (Worthington 2 micrograms per ml) for 30 minutes at 37°C had no effect on the binding of $^3$H-PGA. Preincubation with 1.0 ml of a solution of trypsin for 30 minutes completely inactivated the hog binder factor. All other binder factors are inactivated by a trypsin solution 1:250, 1 mg/ml.

Figure 7:
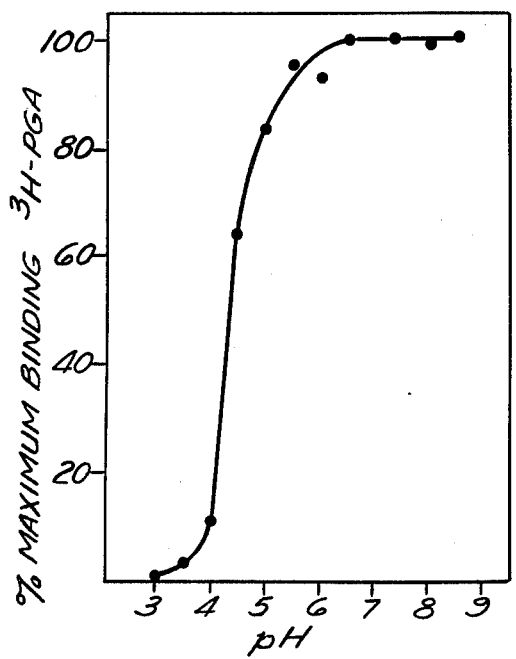
FIG. 7 is a graph showing the effect of pH on the binding of $^3$H-PGA.

The effect of pH on binding is depicted in FIG. 7 utilizing activated charcoal powder coated with albumin for separating bound and free PGA, the point of ½ maximum binding was approximately pH 4.5. There was no significant difference whether the binder or the folate was in excess. No effect on binding at any pH has been observed when several of the common inorganic divalent cations such as calcium, zinc, and magnesium were present at a concentration of 5 mM or when chelating agents such as EDTA (ethyldiamine tetraacetic acid) 20 mM and citrate (10 mM) were added to the incubation mixture. When the binder composition was exposed to 8 M urea or to 6 M guanidine hydrochloride solution, binding activity was lost. However, 8 M urea had no effect on the folate binder complex after it had formed whereas 6 M guanidine hydrochloride could disrupt the complex. This effect of the guanidine hydrochloride was found to be nearly completely reversible.

The rate of PGA binder complex formation with hog kidney binder factor was determined at several temperatures by equilibrating solutions of the binder and of $^3$H-PGA at the appropriate temperature and then combining aliquots of each such that the $^3$H-PGA was in approximately 20% excess to the binding capacity of the hot kidney binder factor composition. The reaction was terminated by the addition of 1.0 ml of ice cold suspension of powdered activated charcoal coated with albumin. This latter step was found to be a very rapid and effective means for stopping the binding reaction. The initial rate of binding at 37°C was found to be 2.5% per second; at 21°C, 1.3% per second; and at 4°C, about 0.65% per seocnd. There was no significant disassociation of the $^3$H-PGA binder complex after one hour at 37°C even when a 50-fold excess of unlabeled PGA was added after the complex had formed.

Although a higher specific activity of the binder was obtained when the initial extraction contained 2-mercaptoethanol, the presence of this agent at concentrations of $10^{-7}$ to $10^{-1}$ M had no effect on the binding reaction with partially purified hog kidney binder factor composition. Because of the reddish color of the hog kidney folate binder extract and because the binder from milk after fractionation of DEAE (diethylamino ethyl cellulose, a standard anion exchange resin) showed strong absorbance at 420 nm, the possibility that iron was involved in the binding by hog kidney preparations was tested. At concentrations up to $2.0 \times 10^{-6}$ M o-phenanthroline, an iron chelating agent, had no effect upon the binding reaction. By elution procedures, both saturated and unsaturated hog kidney binder factor show an apparent molecular weight of 35,000 to 40,000 daltons.

As indicated above, high affinity folate binder factors have also been observed in bovine milk, in serum and leukocytes of patients with leukemia, in normal and in folate-deficient serum; in addition, a lower affinity folate binder factor has been reported in the brush border of intestinal mucosa. Because of the special properties described above and because of the relative ease and economy with which it can be obtained, the hog kidney folate binder factor appears to offer the best material for assay purposes and for study and comparison with binders of folates from other sources. One of the highly significant discoveries resulting from this work has been the detection of bound folate in human serum. Although this is very low in normal patients such that it can, in such cases, be ignored, the amount of bound folate which occurs in the human test serum varies with the pathological condition of the patient and may thus be used as a diagnostic aid. It may, therefore, be suggested that, regardless of the method for assaying serum folate, whether it be by the herein described method, the Rothenberg method, or the L. casei method, an accurate assay must take account of the amount of bound folate which occurs in the test serum.

What is claimed is:
1. A competitive radioisotopic assay for measuring the concentraion of folate in serum comprising the steps of:
   a. radioisotopically relating the bound amounts of a labeled folate and a known folate at various concentrations of the known folate in a first system containing a predetermined amount of the labeled folate, a predetermined amount of a binder factor for the folates, and a predetermined amount of defolated test serum;
   b. radioisotopically determining the bound amount of said labeled folate in a second system containing said predetermined amount of labeled folate, the test serum, and said predetermined amount of said binder factor; and
   c. correlating the bound amount of labeled folate determined in step (b) through the relationship determined in step (a) to ascertian the amount of folate in the serum.
2. A method in accordance with claim 1 wherein the labeled folate and the known folate are blended together before addition of the binder factor.
3. A method in accordance with claim 2 wherein the mixture of the labeled folate and the known folate are incubated for from 30 to 60 minutes prior to addition of the binder factor.
4. A method in accordance with claim 1 wherein the labeled folate and the known folate in step (a) and the labeled folate and the test serum in step (b) are blended together prior to addition of the binder factor in each of said steps.
5. A method in accordance with claim 1 wherein the defolated serum is pooled normal human serum.
6. A method in accordance with claim 1 in which the defolated serum is defolated by contact with activated carbon.
7. A method in accordance with claim 1 wherein the test serum is denatured prior to step (b) to remove serum folate binders.
8. A method in accordance with claim 6 wherein the test serum is denatured by heating to the boiling point of water, settled, and the supernatant liquid used as the test serum.

9. A method in accordance with claim 1 wherein the folate binder factor is hog kidney folate binder factor.
10. A method in accordance with claim 1 in which the labeled folate is $^3$H-pterolymonoglutamate.
11. A method in accordance with claim 1 in which the known folate is d, 1,5-methyltetrahydrofolic acid.
12. A method in accordance with claim 1 in which
   1. the labeled folate and the known folate in step (a) and the labeled folate and the test serum in step (b) are blended together prior to additon of the binder factor in each of said steps;
   2. the defolated serum is pooled normal human serum which has been defolated by contact with activated carbon;
   3. the folate binder factor is hog kidney folate binder factor;
   4. the labeled folate is $^3$H-pteroylmonoglutamate; and
   5. the known folate is d, 1,5-methyltetrahydrofolic acid.
13. A competitive radioisotopic assay for measuring the bound pool of folate in serum comprising the steps of:
   a. radioisotopically relating the bound amounts of a labeled folate and a known folate at various concentrations of the known folate in a first system containing a predetermined amount of the labeled folate, a predetermined amount of a binder factor for the folates, and a predetermined amount of defolated test serum;
   b. radioisotopically determining the bound amount of said labeled folate in a second system containing said predetermined amount of labeled folate, the test serum, and said predetermined amount of said binder factor;
   c. radioisotopically determining the bound amount of said labeled folate in a third system containing said predetermined amount of labeled folate, denatured test serum, and said predetermined amount of said binder factor;
   d. correlating the bound amount of labeled folate determined in step (b) through the relationship determined in step (a) to ascertain the amount of free folate in the serum;
   e. correlating the bound amount of labeled folate determined in step (c) through the relationship determined in step (a) to ascertain the total amount of folate in the serum; and
   f. determining the amount of bound pool of folate in serum by subtracting from the result obtained in step (e) the result obtained in step (d).
14. A process for producing a binder factor for folic acid and derivatives thereof from animal organs which comprises the steps:
   a. homogenizing the animal organ in an aqueous medium;
   b. extracting a binder factor containing moiety with aqueous citric acid solution at a pH less than 4;
   c. ethanol extracting the binder factor in dilute ethanol to precipitate protein at pH 7;
   d. precipitating the binder factor by concentrating the ethanol; and
   e. recovering the precipitated binder factor.
15. A binder factor for folic acid and derivatives thereof produced in accordance with claim 14.
16. A process in accordance with claim 14 wherein the citric acid solution contains 5.0 mM of 2-mercaptoethanol.

* * * * *

UNITED STATES PATENT OFFICE
CERTIFICATE OF CORRECTION

Patent No. 3,972,991  Dated August 3, 1976

Inventor(s) Jesse Douglas Caston et al.

It is certified that error appears in the above-identified patent and that said Letters Patent are hereby corrected as shown below:

Column 4, line 13, "19670" should be --1967)--.

Column 5, line 5, "constnat" should be --constant--.

Column 8, line 56, "th" should be --the--.

Column 10, line 30, "(FIG. 6" should be --(FIG. 6A--.

Column 12, line 50 "seocnd" should be --second--.

Signed and Sealed this

Thirtieth Day of November 1976

[SEAL]

Attest:

RUTH C. MASON
Attesting Officer

C. MARSHALL DANN
Commissioner of Patents and Trademarks